United States Patent [19]

Miller et al.

[11] 4,241,175
[45] Dec. 23, 1980

[54] ASSAY FOR HEPATITIS B CORE ANTIBODY

[75] Inventors: William J. Miller, North Wales; William J. McAleer, Ambler; Lynn T. Callahan, North Wales, all of Pa.

[73] Assignee: Merck & Co., Inc., Rahway, N.J.

[21] Appl. No.: 970,721

[22] Filed: Dec. 18, 1978

[51] Int. Cl.$^3$ .............................................. C12Q 1/66
[52] U.S. Cl. ...................................... 435/7; 435/287; 435/810
[58] Field of Search ................... 435/7, 188, 287, 810; 429/12; 23/230 B

[56] References Cited

U.S. PATENT DOCUMENTS

| | | | |
|---|---|---|---|
| 3,551,555 | 12/1970 | Schuurs | 424/12 |
| 3,654,090 | 4/1972 | Schuurs et al. | 424/12 |
| 3,995,019 | 11/1976 | Jerome | 424/12 |
| 4,100,267 | 7/1978 | Shaw | 424/12 |
| 4,102,996 | 7/1978 | McAleer et al. | 435/7 |
| 4,148,869 | 4/1979 | Deaton | 435/7 |
| 4,157,280 | 6/1979 | Halbert et al. | 424/12 |

OTHER PUBLICATIONS

Purcell et al, "Radioimmunoassay for the Detection of the Core of the Dane Particle and Antibody to It", *Intervirology*, vol. 2 (1973/1974) pp. 231-243.

Mathiesen, et al, "Enzyme-Linked Immunosorbent Assay for Detection of Hepatitis A Antigen in Stool and Antibody to Hepatitis A Antigen in Sera: Comparison with Solid-Phase Radioimmunoassay, Immune Electron Microscopy, and Immune Adherence Hemagglutination Assay", *J. Clin. Micro.*, vol. 17, No. 2, (1978), pp. 184-193.

*Primary Examiner*—Thomas G. Wiseman
*Attorney, Agent, or Firm*—Donald J. Perrella; Julian S. Levitt

[57] ABSTRACT

HB$_c$Ab is detected in biological fluid by contacting HB$_c$Ag derived from Dane particles and adhered to a surface with the biological fluid and an antibody-enzyme conjugate. The HB$_c$Ag is adhered to the surface in the presence of a nonionic surfactant.

10 Claims, No Drawings

ASSAY FOR HEPATITIS B CORE ANTIBODY

BACKGROUND OF THE INVENTION

The presence of hepatitis B core antibody ($HB_cAb$) in biological fluids is a diagnostic marker of current or previous hepatitis B disease. Biological material such as, e.g, serum or plasma from such individuals also may contain hepatitis B surface antigen ($HB_sAg$) or Dane particles in levels capable of transmitting disease although below levels detectable in presently available assays. A difficulty with tests heretofore known for $HB_cAb$, e.g., RIA or IAHA, is their short shelf life of only a few weeks and in the case of the IAHA assay the requirement for specialized red blood cells which are difficult to obtain.

OBJECTS OF THE INVENTION

It is, accordingly, an object of the present invention to provide an improved assay for $HB_cAb$. Another object is to provide an assay having a shelf life of over one year. A further object is to provide an enzyme immunoassay for $HB_cAb$. These and other objects of the present invention will be apparent from the following description.

SUMMARY OF THE INVENTION $HB_cAb$ is detected in biological fluid by contacting $HB_cAg$ derived from Dane particles and adhered to a surface with the biological fluid and an antibody-enzyme conjugate. The $HB_cAg$ is adhered to the surface in the presence of a nonionic surfactant.

DETAILED DESCRIPTION

The present invention relates to an assay for detecting hepatitis B core antibody ($HB_cAb$) in biological fluid and, more particularly, to an enzyme linked assay for detecting $HB_cAb$ in biological fluid, especially human biological fluid.

According to the present invention hepatitis B core antigen ($HB_cAg$) which may be obtained as described in U.S. Pat. No. 4,102,996 issued July 25, 1978 to William J. Miller et al. is attached to a surface either by first contacting the surface with bovine serum albumin (BSA) and a nonionic surfactant followed by the $HB_cAg$ or by simultaneously contacting the surface with BSA, $HB_cAg$, and the nonionic surfactant. After incubation at elevated temperature of from about 32° to about 42° C. for several hours, typically from about 8 to about 25 hours, to coat the surface with the $HB_cAg$, the surface is drained, washed and contacted simultaneously with the sample of human biological fluid to be tested for presence of $HB_cAb$ and with an $HB_cAb$-enzyme conjugate. The latter is prepared in known manner, e.g. by the method described by Engvall et al., *J. Immunol.*, 109, No. 1, 129 (1972). The mixture is incubated for from about 0.5 hour to about 2 hours at from about 35° to about 39° C. and then washed. An enzyme substrate solution is added followed by a second incubation under the same conditions as the previous one. The optical density of the solutions are then measured at 400 nm. Readings below the midpoint are scored positive; readings above the midpoint are scored negative. The midpoint is calculated by dividing the difference between the negative and positive controls by 2, and adding to the result the value of the positive control.

It has been found that the ability of the $HB_cAg$ derived from Dane particles to adhere to the surface occurs only in the presence of a nonionic surfactant. This is unexpected and surprising as the presence of such surfactants is known to prevent adherence of proteinaceous materials such as $HB_cAg$. See Engvall et al., supra. Further the ability of the $HB_cAg$ to adhere to the surface in the presence of BSA is again unexpected and surprising as BSA would be expected to compete for the attachment sites. See Hoffman, J. Allerg. Clin. Immunol., 51, No. 5, 303 (1973).

The nonionic surfactant has from about 15 to about 35 oxyethylene units, preferably from about 18 to about 33 oxyethylene units. Suitable nonionic surfactants are oxyethylated alkyl phenols, polyoxyethylene sorbitan fatty acid esters, polyoxyethylene acids, polyoxyethylene alcohols, polyoxyethylene oils and polyoxyethylene oxypropylene fatty acids. Some specific examples are the following:

alkylphenoxypolyethoxy (30) ethanol
polyoxyethylene (20) sorbitan monolaurate
polyoxyethylene (20) sorbitan monopalmitate
polyoxyethylene (20) sorbitan monostearate
polyoxyethylene (20) sorbitan tristearate
polyoxyethylene (20) sorbitan monooleate
polyoxyethylene (20) sorbitan trioleate
polyoxyethylene (20) palmitate
polyoxyethylene (20) lauryl ether
polyoxyethylene (20) cetyl ether
polyoxyethylene (20) stearyl ether
polyoxyethylene (20) oleyl ether
polyoxyethylene (25) hydrogenated castor oil
polyoxyethynene (25) oxypropylene monostearate.

The following examples illustrate the present invention without, however, limiting the same thereto. All temperatures are expressed in degrees Celsius.

EXAMPLE 1

To each of five wells of a polystyrene multi-well assay plate wherein each well has a volume of about 0.3 ml there is added 0.20 ml of phosphate buffered saline (PBS) containing 0.1% (vol/vol) of polyoxyethylene (20) sorbitan monooleate. The solution is decanted after remaining in the wells for one hour at 37°. To the empty wells there is added 0.2 ml of a PBS solution containing 0.1% (wt/vol) bovine serum albumin (BSA) and having suspended therein $HB_cAg$ having an IAHA titer of 1:8. This $HB_cAg$ is obtained according to the procedure of Example 1C of U.S. Pat. No. 4,102,996. The wells are covered and incubated at 37° for 18 hours. The antigen solutions are decanted and the empty wells are washed 3 times with 0.25 ml of the PBS solution described above. The serum to be tested is diluted 1:50, 1:500 and 1:5,000 in the PBS solution described above.

0.1 Ml of each diluted serum is added to 0.1 ml of a $HB_cAb$ alkaline phosphatase conjugate and transferred into three coated wells. A negative control is obtained by adding to a fourth coated well 0.1 ml of the PBS buffer described above and 0.1 ml of the $HB_cAb$ alkaline phosphatase conjugate. A positive control is obtained by adding to a fifth coated well 0.1 ml of 1:50 dilution of $HB_cAb$-containing serum of known titer and 0.1 ml of the $HB_cAb$ alkaline phosphatase conjugate. The plate is covered and incubated for 1 hour at 37°. The liquid in the plates is decanted and the plates washed 3 times with 0.25 ml of the PBS solution described above. To all 5 wells there is added 0.2 ml of substrate solution composed of 1 mg/ml of p-nitrophenyl phosphate dissolved in 0.54% (wt/vol) Na$_2$CO$_3$ buffer, pH 9.8, containing 0.02% (wt/vol) MgCl$_2$.6H$_2$O. This mixture is incubated at 37° for 1 hour and the optical density measured at 400 nm. The following results are obtained:

| Well | Serum Dilution | O.D. | Results (Positive or Negative with respect to mid-point*) |
|---|---|---|---|
| 1 | 1:50 | 0.10 | + |
| 2 | 1:500 | 0.10 | + |
| 3 | 1:5,000 | 0.80 | − |
| 4 (neg. Control) | | 1.0 | − |
| 5 (Pos. Control) | | 0.05 | + |

*Calculation of Midpoint $$\frac{1.0 - 0.05}{2} = 0.475 + 0.05 = 0.525 = \text{Midpoint}$$

EXAMPLE 2

The procedure of Example 1 is repeated except that the initial step of coating the wells with polyoxyethylene (20) sorbitan monooleate is omitted and the PBS solution of Example 1 is modified by the addition of 1% (vol/vol) polyoxyethylene (20) sorbitan monooleate. Similar results are obtained.

EXAMPLE 3 (Comparative)

The procedure of Example 1 is repeated except that the initial step of coating the wells with polyoxyethylene (20) sorbitan monooleate is omitted. The following optical densities are observed:

| Well | O.D. |
|---|---|
| 1 | 0.1 |
| 2 | 0.1 |
| 3 | 0.1 |
| 4 | 0.1 |
| 5 | 0.05 |

These results indicate that the HB$_c$Ag did not adsorb to the surface of the well.

A similar failure of the HB$_c$Ag to absorb to the surface of the well is observed when the procedure of Example 2 is repeated except eliminating polyoxyethylene (20) sorbitan monooleate from the PBS solution.

What is claimed is:

1. A method for determining the presence of hepatitis B core antibody (HB$_c$Ab) in biological fluid comprising
   (a) directly adhering hepatitis B core antigen (HB$_c$Ag) derived from Dane particles to a solid surface wherein HB$_c$Ag is adhered to the surface by adsorption in the presence of an amount of a nonionic surfactant having from about 15 to about 35 oxyethylene units effective to cause adherence,
   (b) contacting the surface with the biological fluid,
   (c) contacting the surface with a hepatitis B core antibody (HB$_c$Ab)-enzyme conjugate,
   (d) contacting the surface with an enzyme substrate solution, and
   (e) measuring the optical density after development of the enzyme substrate solution.
2. A method according to claim 1 wherein the biological fluid is blood, plasma or serum.
3. A method according to claim 2 wherein the biological fluid is plasma.
4. A method according to claim 1 wherein the nonionic surfactant is polyoxyethylene (20) sorbitan monooleate.
5. A diagnostic reagent comprising a solid surface having directly adhered thereto hepatitis B core antigen (HB$_c$Ag) derived from Dane particles wherein HB$_c$Ag is adhered by adsorption in the presence of a nonionic surfactant having from about 15 to about 35 oxyethylene units present in an amount effective to cause adherence.
6. A diagnostic reagent according to claim 5 wherein the nonionic surfactant is an oxyethylated alkyl phenol, polyoxyethylene sorbitan fatty acid ester, polyoxyethylene acid, polyoxyethylene alcohol, polyoxyethylene oil, or polyoxyethylene oxypropylene fatty acid.
7. A diagnostic reagent according to claim 5 wherein at least part of the HB$_c$Ag is complexed with hepatitis B core antibody (HB$_c$Ab).
8. A diagnostic reagent according to claim 5 wherein at least part of the HB$_c$Ag is complexed with an HB$_c$Ab-enzyme conjugate.
9. A diagnostic reagent according to claim 5 wherein at least part of the HB$_c$Ag is complexed with HB$_c$Ab and at least part of the HB$_c$Ag is complexed with an HB$_c$Ab-enzyme conjugate.
10. A diagnostic reagent according to claim 7 wherein the enzyme is alkaline phosphatase.

* * * * *